United States Patent
Peplow et al.

(10) Patent No.: US 7,297,342 B2
(45) Date of Patent: Nov. 20, 2007

(54) ORTHOPAEDIC MATERIALS DERIVED FROM KERATIN

(75) Inventors: Philip Victor Peplow, Dunedin (NZ); Subasinghe Nisanke George Premalal Jayantha Dias, Dunedin (NZ); Alisa Dawn Roddick-Lanzilotta, Christchurch (NZ); Robert James Kelly, Christchurch (NZ)

(73) Assignee: Keratec Limited, Lincoln, Canterbury (NZ)

( * ) Notice: Subject to any disclaimer, the term of this patent is extended or adjusted under 35 U.S.C. 154(b) by 0 days.

(21) Appl. No.: 10/517,378

(22) PCT Filed: Jun. 10, 2003

(86) PCT No.: PCT/NZ03/00116

§ 371 (c)(1), (2), (4) Date: Jun. 15, 2005

(87) PCT Pub. No.: WO03/103737

PCT Pub. Date: Dec. 18, 2003

(65) Prior Publication Data

US 2005/0232963 A1 Oct. 20, 2005

(30) Foreign Application Priority Data

Jun. 10, 2002 (NZ) .................... 519456

(51) Int. Cl.
*A61F 2/28* (2006.01)
*A61K 38/17* (2006.01)
(52) U.S. Cl. ..................... 424/423; 350/357
(58) Field of Classification Search ........ 424/443, 424/486, 423; 530/357; 623/23.63
See application file for complete search history.

(56) References Cited

U.S. PATENT DOCUMENTS

| | | | |
|---|---|---|---|
| 5,972,385 A | 10/1999 | Liu et al. | 424/486 |
| 2001/0018614 A1 | 8/2001 | Bianchi | 623/16.11 |
| 2002/0013408 A1 | 1/2002 | Rhee et al. | 525/54.1 |
| 2002/0183858 A1 | 12/2002 | Contiliano et al. | 623/23.76 |
| 2003/0039676 A1 | 2/2003 | Boyce et al. | 424/423 |

FOREIGN PATENT DOCUMENTS

| | | |
|---|---|---|
| FR | 2 687 577 A1 | 8/1993 |
| JP | 63-229058 | 9/1988 |
| WO | WO 99/19005 | 4/1999 |
| WO | WO 99/26570 | 6/1999 |

OTHER PUBLICATIONS

Marshall, R. C., et al., "Structure and Biochemistry of Mammalian Hard Keratin", Electron Microsc. Res., vol. 4, pp. 47-83, 1991.
Yamaguchi, K., et al., "Cultivation of Fibroblast Cells on Keratin-Coated Substrata", J. Biomater. Sci., Polymer Edn., vol. 9, No. 3, pp. 259-270 (1998).

*Primary Examiner*—Maryam Monshipouri
*Assistant Examiner*—Marsha Tsay
(74) *Attorney, Agent, or Firm*—Bacon & Thomas, PLLC

(57) ABSTRACT

The invention provides a biocompatible material derived from keratin that is useful for many aspects of medical treatment of bone. The keratin material is preferably S-sulfonated and enriched in intermediate filament proteins of high molecular weight. The keratin material may be porous for use as a bone replacement and augmentation product but also provided is the use of dense keratin materials in bone treatment for use as an internal fixation appliance in the treatment of bone fractures and bone regeneration, and a method for preparing the keratin material for use in the preservation, restoration and development of form and function of bone.

3 Claims, No Drawings

ORTHOPAEDIC MATERIALS DERIVED FROM KERATIN

The present application is a 35 U.S.C. §371 application of PCT/NZ03/00116, filed Jun. 10, 2003, which claims priority from New Zealand Application No. 519456, filed Jun. 10, 2002.

FIELD OF THE INVENTION

This invention relates to the preparation of medical materials from keratins derived from animal sources such as wool, hair, horns, hooves, and scales. The keratin materials described are biocompatible, biointegratable, and biodegradable and the primary application of the materials is in orthopaedic surgery for replacement and augmentation of bone, and fixation and immobilization of bone fractures and bone segments.

BACKGROUND TO THE INVENTION

Keratins are a class of structural proteins widely represented in biological structures, especially in epithelial tissues of higher vertebrates. Keratins may be divided into two major classes, the soft keratins (occurring in skin and a few other tissues) and the hard keratins (forming the material of nails, claws, hair, horn, feathers and scales).

The toughness and insolubility of hard keratins, which allow them to perform a fundamental structural role in many biological systems, are the desirable characteristics found in many of the industrial and consumer materials derived from synthetic polymers. In addition to possessing excellent physical properties, keratin, as a protein, is a polymer with a high degree of chemical functionality and consequently exhibits many properties that synthetic polymers cannot achieve. Keratin is therefore, well suited to the development of medical products with high-value, niche market applications. Medical materials which are absorbed (resorbed) by the body tissues after fulfilling their function are an example of an area of high value products in which the specific characteristics of keratin allow it to outperform both natural and synthetic competitive materials.

Yamauchi (K. Yamauchi, M. Maniwa and T. Mori, Journal of Biomaterial Science, Polymer edition, 3, 259, 1998) demonstrate that keratins can be processed into matrices that are considered biocompatible by virtue of their in vitro and in vivo properties. The processing methods used to make these materials require large concentrations of reducing agents, such as thiols, and processing conditions that are not suitable for commercial production of materials.

Kelly (WO03/19673) shows that keratins can be processed into complex shapes using commercially viable chemistries and processing conditions.

Blanchard (U.S. Pat. No. 5,358,935 and U.S. 2003/0035820A1) demonstrates that keratins can be extracted from human hair using high concentrations of reductants, or harsh oxidants, and processed to produce materials useful in some soft tissue applications. However, extraction and reconstitution methods are harsh and cause degradation to the keratin, through irreversible oxidation of the distinctive keratin amino acid cystine to cysteic acid, or through exposure of the protein to high pH conditions that lead to peptide hydrolysis. This results in many beneficial characteristics of the protein being lost, in particular the toughness necessary for hard tissue applications.

In order to produce keratin biomaterials suitable for orthopaedic applications, methods of processing are needed that maintain the keratin characteristics and provide materials with good toughness properties. This invention describes such materials and their methods of production.

U.S. Pat. No. 6,432,435 claims a tissue engineering scaffold having a keratin with hydrophilic groups, the keratin being bound with keratin-keratin disulfide bonds. The patent however provides no disclosure as to how a sulfonated keratin can be incorporated into a hard tissue such as bone. The examples provided all relate to its use in soft tissue or porous structures.

The present inventors have found that keratin can be incorporated into hard tissue such as bone and hence used in the treatment of bone injury.

Many tissues of the body including bone are continually renewed. New bone matrix (which will become mineralized) is laid down principally by specific cells called osteoblasts, and the different components of bone are removed by osteoclasts. An implanted material which is removed and replaced with bone tissue by this biological process will have a greater advantage over those materials which break down by other mechanisms within the body e.g. chemical degradation. It is desirable that new bone is formed juxtaposed to the surface of the implanted material, thereby integrating this material into the tissue until it is completely resorbed and replaced.

Bone may be categorized into four microstructural components: cells, organic matrix, inorganic matrix, and soluble signalling factors. Osteoblasts are metabolically active secretory cells that express soluble signalling factors and osteoid, a product whose extracellular modification yields an organic insoluble substratum consisting mostly of type I collagen. Expression of these products by osteoblasts occurs during maintenance (e.g. remodelling), and repair of bone. Monocyte-macrophage precursors found in the bone marrow enter the circulation, and through asynchronous fusion produce a multinucleated cell up to 100 microns in diameter with an average of 10 to 12 nuclei, known as an osteoclast. Osteoclasts have a ruffled border and this constitutes the resorptive territory of the osteoclast where enzymatic breakdown of the bone surface occurs. The term 'remodelling' is used to describe the dynamic events associated with bone repair and homeostasis in the mature individual. The sum of the processes associated with homeostatic remodelling is known as activation-resorption-formation. Osteoblasts are activated by signalling factors and vacate an area of bone; osteoclasts become stimulated, home in to the osteoblast-vacant zone, attach, resorb, and, in response to an as yet unidentified signal, cease resorbing and abandon their attachment. Osteoclastic resorptive pits become repopulated by a contingent of osteoblasts that express osteoid, which calcifies, restoring bone. In humans, the activation-resorption-formation processes take between 3 and 6 months.

Following an insult to bone (e.g. fracture or surgical removal of a tumor) there is extensive bleeding and in 2 to 5 days the haemorrhage forms a large blood clot. Neovascularization begins to occur peripheral to this blood clot. There is also the standard inflammatory response occurring in the surrounding soft tissues leading to polymorphonuclear leucocytes, macrophages, and mononuclear cells accumulating in the periphery of the clot. By the end of the first week, most of the clot is organised by invasion of blood vessels and early fibrosis. The earliest bone (woven bone) is formed after 7 days. Since bone formation requires a good blood supply, the woven bone spicules begin to form at the periphery of the clot where vascularisation is greatest. Pluripotential mesenchymal cells from the surrounding soft tissues and from within the bone marrow give rise to osteoblasts that synthesize the woven bone. Frequently cartilage is also formed and eventually is replaced by endochondral ossification. The granulation tissue containing bone-cartilage is termed a callus (Inflammatory phase).

After the first week, the next stage begins and extends for several months, depending upon the degree of movement and fixation. By this stage, the acute inflammatory cells have dissipated and the reparative process involving the differentiation of pluripotential cells into fibroblasts and osteoblasts commences. Repair proceeds from the periphery towards the centre and accomplishes two objectives: one, it organises and resorbs the blood clot; and two, more importantly, it furnishes neovascularisation for the construction of the callus, which eventually bridges the bone-deficient site. The events leading to the repair are as follows. Large numbers of osteoclasts from the surrounding bone move into the healing site. New blood vessels accompany these cells supplying nutrients and providing more pluripotential cells for cell renewal. The site is remodelled by osteoclasts (Reparative phase).

In several weeks the callus has sealed the bone ends and remodelling begins, in which the bone is reorganised so that the original cortex is restored (Remodelling phase).

OBJECT OF THE INVENTION

It is an object of the invention to provide a material which contains keratin and which is useful in assisting bone formation and/or which provides the public with a useful choice.

SUMMARY OF THE INVENTION

The invention provides a keratin-containing material for use in preservation, restoration and development of form and function of bone in the skeletal system.

The invention also provides a porous keratin material for use in the replacement and augmentation of bone.

The invention also provides a dense keratin material for use in bone fixation and immobilization.

The keratin is preferably S-sulfonated and more preferably is enriched in intermediate filament protein.

The dense keratin material may be prepared by compression of solid keratin powder or by compression of keratin films.

The material may contain up to 60% calcium salts.

The material may be prepared by compression and freeze-drying of solid keratin.

Alternatively a solution of keratin may be freeze dried.

The invention also provides the use of a keratin material in the preservation, restoration and development of form and function of bone.

The invention also provides a method of forming a porous S-sulfonated keratin enriched material comprising:
a) compressing keratin in the presence of a soluble porogen;
b) removing the porogen and strengthening the material;
c) washing the protein material; and
d) freeze drying the material.

The invention also provides a method of forming keratin material into an orthopaedic product.

The invention also provides a biocompatible material in the form of a porous keratin that is enriched in intermediate filament protein for use in bone replacement/augmentation therapy.

The material may be prepared by compression of solid keratin powder, in the presence of a porogen and compression may be followed by freeze drying. The porogen may be selected from sodium chloride or another biocompatible salt, or glycerol or another biocompatible solvent. The amount and nature of porogen may be controlled to select the pore sizes and allow the infiltration of osteoprogenitor cells to facilitate the colonization of keratin material when implanted. Hydroxyapatite may also be added to the keratin.

The invention also provides a method of forming a dense material of S-sulfonated keratin material into an orthopaedic product comprising:
a) compressing keratin in the presence of heat and water;
b) strengthening the material;
c) washing the material to remove residual chemicals; and
d) drying the material.

The invention also provides a method for forming a dense material of S-sulfonated keratin into an orthopaedic product comprising:
a) strengthening the keratin-containing starting material;
b) washing the material to remove residual chemicals;
c) drying the material; and
d) compressing keratin in the presence of heat and water.

The invention also provides orthopaedic medical materials such as plates, pins and screws manufactured from biocompatible keratin material for treatment of fractures by internal fixation as well as fixation and immobilisation of bone segments.

The invention also provides a method of reforming S-sulfonated keratin enriched in intermediate filament protein into a tough, dense biocompatible material for use as an internal fixation appliance in the treatment of bone fractures.

Moisture and chemicals may be added. The controlled use of reducing agents may be used to remove the sulfonate group from the S-sulfonate keratin and reform disulfides originally present.

The keratin used in the formation of bone can be made by the method according to WO 03/011894 which provides a process for the preparation of keratin derivatives of high molecular weight, whereby the process includes a first stage digestion step of sulfonating a keratin source by oxidative sulfitolysis followed by a second stage repetitive aqueous extraction involving separation of soluble and insoluble keratin and subsequent re-extraction of the insoluble keratin to thereby produce a highly S-sulfonated keratin derivative.

WO 03/018673 provides a foam fibre adhesive material or film derived from S-sulfonated keratin protein. The method involves solvent casting a solution of S-sulfonated keratin protein.

Also provided is a method for making a film, fibre, foam or adhesive material derived from highly S-sulfonated keratin intermediate filament proteins.

The present invention provides a method of making keratin material suitable for use in bone structures and also provides keratin material for use in bone structures based on the methods of WO 03/018673 and WO 03/011894.

A degradable keratin appliance will provide enough flexibility to stimulate new bone growth (unlike some rigid permanent materials currently used) by gradually transferring functional loads to the healing bone. Furthermore subsequent surgery is not needed to remove the keratin-derived fixation appliances or devices.

The method of reforming the S-sulfonated keratin enriched in intermediate filament protein into a tough, dense material for use as an internal fixation appliance in the treatment of bone fractures, may involve compressing the biocompatible protein in the presence of moisture, chemicals, and in some cases heat, to form a desired shape. The formation of crosslinks within the material to ensure strength and toughness under biological conditions occurs during compression, or subsequently through chemical treatment.

The method may also involve the controlled use of reducing agents to remove the sulfonate group from the S-sulfonated keratin and reform the disulfides originally present in the native keratin. This serves the dual purpose of firstly, providing strength and toughness under biological conditions by effectively polymerizing the keratin protein through an extended network of disulfide crosslinks; and secondly, controlling the rate and extent of biodegradation that occurs by impeding enzymatic digestion of the material. By controlling the rate of biodegradation, the invention allows the keratin products to be used in applications where a range of healing times are desirable.

The reconstituted keratin described in this patent specification is completely biocompatible and does not elicit any significant foreign body type immune reaction. The keratin is degraded by the normal processes occurring in bone described above and is replaced with normal bone. Therefore in bone replacement and augmentation, this keratin has similar properties to autologous bone. In the case of treatment of fractures, appliances made of this keratin will have the necessary physical properties to carry out the fixation and immobilization of the bone segments, and once this function is fulfilled the keratin will gradually resorb and eventually disappear from the tissues. During the initial period of resorption, the gradually weakening keratin appliance will stimulate new bone formation by subjecting the bone to increasing functional loads. This will prevent a stress shielding effect which is found with metal appliances. Furthermore the degradation and resorption of keratin is a great advantage compared to metal appliances which are either permanently retained in the body or require a second surgical procedure to remove them.

The invention may be applied to any bone formation function. Form and function of bones can be disrupted by:
  developmental anomalies where bone is under developed, or abnormally developed
  trauma causing either fractures, fracture dislocations, with or without loss of bone
  surgical interventions such as, excision of malignant or benign tumours/tumour-like conditions, or in degeneration conditions of bone
  bone necrosis and destruction caused by conditions such as infections The treatment modalities to these conditions attempt to preserve, restore, or develop the normal form and function of the affected bones of the skeletal system.

The term "intermediate filament proteins" describes keratin proteins from the intermediate filament protein class. Keratin intermediate filaments are derived from hard alpha keratins and generally recognized in the art as comprising of two families of low sulphur polypeptides containing both helical and non-helical segments, as discussed in Marshall et al, Structure and Biochemistry of Mammalian Hard Keratin, Electron Microscopy Review, Vol 4, pp 47-83, 1991.

"Enriched in intermediate filament protein" means that there is more intermediate filament protein in the product than in the corresponding amount of native keratin source.

DESCRIPTION OF PREFERRED EMBODIMENTS OF THE INVENTION

The invention will now be described, by way of example only with reference to the following preferred embodiments.

The features of this invention specifically cite some methods and applications based on hard α-keratins from wool. However, the principle can equally well apply to alternative α-keratins, or any source of keratin which is able to yield proteins of the intermediate filament (IF) type.

Similar preparative methods have been applied by the applicants to other keratin sources such as feathers, to produce materials equally well suited for some of the applications described below. The features of this invention are extended to cover limited areas of the utilisation of such keratins as well, in applications which are not dependent on the presence of proteins of the α-type (IF proteins). This includes applications where preparations based on β or feather keratin may be combined with IF proteins.

Wool represents a convenient source of hard α-keratins, although any other animal fibre, or horns, or hooves, would serve equally well as a source of the desired proteins. Wool is composed of approximately 95% keratin, which can be broadly divided into three protein classes. The intermediate filament proteins are typically of high molecular weight (45-60 kD), with a partly fibrillar tertiary structure and a cysteine content of the order of 6%. They account for approximately 58% of the wool fibre by mass although only part of this mass is actually helix-forming in structure. The high- and ultra-high-sulphur proteins, approximately 26% of the wool fibre, are globular in structure, have a molecular weight range of 10-40 kD and can contain cysteine levels up to 30 mol %. The high-glycine-tyrosine proteins are a minor class comprising 6% of the wool fibre, have molecular weights of the order of 10 kD and are characterised by their high content of glycine and tyrosine amino acid residues.

Proteins from the different classes of wool keratins possess characteristics that will give them unique advantages in specific applications.

This invention pertains largely to the use of intermediate filament proteins, and the use of them to produce materials for use in orthopaedic surgery Nonetheless the other non-fibrillar proteins have applications in their own right in more restricted fields.

Highly S-sulfonated keratin, derived from an animal source such as those described, when purified to isolate the intermediate filament protein component, is a biocompatible/biodegradable material ideal for use in a range of products for orthopaedic use. The keratin may be prepared by methods such as those outlined in WO 03/011894. The S-sulfonated keratin proteins themselves may be made according to methods in WO 03/018673. These methods result in the cystine present in the original keratin source being modified to become S-sulfocysteine. This group is highly polar and can lead to the derivatised keratin becoming soluble under aqueous conditions at pH>4. In addition the S-sulfonated material is responsive to moisture and suitable for processing into matrices useful in orthopaedic care. In some cases It is useful to retain the S-sulfonate functionality, whereas for other matrices it is useful to chemically treat the protein as part of a reconstitution process to remove the S-sulfonate functionality and restore the disulfide bonds originally present within the keratin. As well as being highly polar and therefore responsive to moisture, the presence of S-sulfo derivatisation renders reconstituted keratin materials susceptible to enzymatic degradation by the proteolytic enzymes present in vivo. Conversion of the S-sulfo groups to cystine renders the prepared keratin materials insoluble and also imparts a degree of resistance to proteolytic enzymes. The cystine containing materials are therefore degraded at a slower rate within the body, a performance characteristic that is important in some orthopaedic applications.

The conversion of S-sulfocysteine to cystine can occur through the application of reducing agents, typically thiol containing solutions such as ammonium thioglycollate, or through methods such as those described in WO 03/018673.

As a proteinaceous material, keratin is well suited as a material used for the creation of orthopaedic care materials which incorporate osteogenic agents, such as the well documented osteogen hydroxyapatite. Reconstituted keratin materials can be readily prepared containing hydroxyapatite at levels from 0-60%, depending on the method of reconstitution. The beneficial healing effects of hydroxyapatite inclusion in biomaterials is well documented, and also demonstrated as part of this invention.

In one embodiment of the invention the S-sulfonated keratin is reconstituted into a porous material for use as a bone replacement or augmentation product. This is achieved by compressing the keratin protein in the presence of water and a soluble porogen, such as sodium chloride. Generally, S-sulfonated keratin intermediate ground to a particle size to aid powder compression, preferable of 125-200 micron, is mixed with water in the ratio from 1:0.1 to 1:10, preferably 1:1, and also sodium chloride in the ratio 1:0.01 to 1:10. Hydroxyapatite is also incorporated into this mixture at a level of 0-60% by mass, preferably 0-10%. This mixture is packed into a die and pressed to a pressure in the range 10,000 to 50,000 kPa for a time in the range 1-30 minutes. On removal from the die a cylinder is cut from the pellet and the cylinder is soaked in a chemical treatment solution, in order to wash out the porogen and leave a porous material, while also removing the sulfonate functionality from the keratin and restoring disulfide crosslinks to the protein. This chemical treatment may take one of two forms. Firstly, a solution of ammonium thioglycollate preferably of concentration 0.25M, containing sodium phosphate, preferably of concentration 0.1M buffered to pH 7.0 can be used to treat the cylinder for a period of from 2-48 hours, preferably 18 hours. Residual chemicals are removed by subsequent washing of the pellet in water. After washing the cylinder is then freeze dried. Alternatively, the cylinder can be subjected to chemical treatment in a solution containing thioglycollic acid, preferably 0.1M for 2-48 hours, preferably 18 hours. Following a brief wash in water, residual chemicals are removed by washing the cylinder in a buffered solution 48-96 hours. The solution is refreshed every 24 hours. Following a further wash in water the cylinder is freeze dried.

The pore size in the material can be controlled by varying the quantity of sodium chloride used in the preparation. For example; typical pore size for a preparation using 0.06 g of sodium chloride per gram of protein is 50-150 microns, whereas 0.14 g of sodium chloride per gram of protein results in pores of up to 320 microns.

The biological properties of the porous keratin material prepared using the thioglycollic acid method are demonstrated both in vitro and in vivo. In vitro, the material is not cytotoxic and supports the growth of human and sheep fibroblasts. Direct contact of the porous material with cells, as described in ISO 10993-5, using sheep fibroblasts produced the following effects. Wells of polystyrene cell culture plates containing either the porous material or no material as a control were initially seeded with ~10,000 cells (0 hours). During the first 24 h post-seeding, the cultures experienced a lag time as evidenced by a decline in cell numbers. This phenomenon has been recognised in all assays-performed and the drop is observed in control wells in addition to those containing the test materials. Experimentation has shown that this lag time lasts for less than 12 h and that the exponential phase of growth begins at this point. Population doublings occur approximately every 24 h-48 h with sub-confluency (approximately 80% confluency) marking the end of logarithmic growth. This corresponds to the end of the experimental time course (5 days or 120 h). Extended time-course experiments have indicated a plateau in cell growth shortly after this with full confluence of the culture. Contact inhibition and depletion of nutrients play a key role in limiting the growth rate at this point and the monolayer culture exhibits signs of cell death (i.e. loss of membrane integrity, reduction in cell numbers, vacuolisation of individual cells). During the assay, cells were witnessed to attach to the upper surface of the disks. By light microscopy, the morphological appearance of these cells was deemed similar on all substrates compared to the no-material control. Similar assays with human fibroblasts produced very similar results, with typical fibroblast growth curves occurring in the presence of the porous material and approximately 80% confluency reached after 120 hours in culture. The control wells had reached 100% confluency at this time.

The in vivo study involved the keratin material treated by the above method, and also a composite of this material containing 6% hydroxyapatite, and manufactured as rods 3 mm diameter, 3 mm length and sterilized by gamma radiation (2.8 Mrads) being implanted into the midshaft (cortical bone) and proximal and distal ends (cortico-cancellous bone) of the long bones of the hind limbs of adult sheep. The tissue responses to the implanted material were studied by histological examination of biopsy samples at 10 days, 3, 6, 8, 12 and 24 weeks. The bone tissue response to the material prepared using thioglyciollic acid showed minimal foreign body type immune reaction to the presence of the implant and there was only a thin layer of granulation tissue (leading to fibrosis) formed between the implant and the surrounding bone. Within 3 to 6 weeks the implant material was colonized by osteoid tissue leading to the laying down of woven bone in the spaces created by resorption of the keratin implant material, and the new bone was joined to the surrounding bone at around 6 to 8 weeks. From 6 weeks onwards remodelling of woven bone into corticocancellous bone occurred. The continuation of this process led to complete integration of the implant material which was replaced by mature bone, and the bone defect was completely healed.

Furthermore the physical properties of this porous material were investigated by manufacturing it in the form of plates 12 mm length, 4 mm width, 3 mm depth and implanted subcutaneously in the sheep. The data obtained by testing the plates on an Instron machine showed that the tensile properties weakened by approximately 10% over a period of 3 to 6 weeks. This was consistent with a loss in dry weight of about 10% at this time. These findings support the ability of this material to stimulate new bone formation and prevent stress shielding, and gradual resorption of this material.

Porous keratin material are also prepared by freeze drying an aqueous solution of S-sulfonated keratin, using methods such as those described in WO 03/018673, and these materials are suitable for use in bone graft applications. A porous keratin material containing a high proportion of hydroxyapatite is prepared from an aqueous solution of S-sulfonated keratin, preferably 5%, by suspending insoluble hydroxyapatite in the keratin solution at a ratio from 1:0.1 to 1:2 keratin to hydroxyapatite mass, preferably 1:1. Upon freezing and subsequent freeze drying an intimate mixture of keratin and hydroxyapatite is created, in a porous sponge material suitable for use in bone graft products.

In another embodiment of the invention the S-sulfonated keratin is reconstituted into a tough, dense material for use as a bone fixation product. This is achieved by compressing the keratin protein. Generally, S-sulfonated keratin ground to a particle size to aid powder compression, preferable of 125-200 micron, is mixed with water in the ratio from 1:0.1 to 1:10, preferably 1:1. Hydroxyapatite is also incorporated into this mixture at a level of 0-60% by mass, preferably 0-10%. This mixture is packed into a die and pressed to a pressure in the range 10,000 to 50,000 kPa for a time in the range 1-30 minutes. On removal from the die a cylinder is cut from the pellet and the cylinder is soaked in a chemical treatment solution, in order to wash out the porogen and leave a porous material, while also removing the sulfonate functionality from the keratin and restoring disulfide crosslinks to the protein. This chemical treatment may take one of two forms. Firstly, a solution of ammonium thioglycollate preferably of concentration 0.25M, containing sodium phosphate, preferably of concentration 0.1M buffered to pH 7.0 can be used to treat the cylinder for a period of from 2-48 hours, preferably 18 hours. Residual chemicals are removed by subsequent washing of the pellet in water. After washing the cylinder is then freeze dried. Alternatively, the cylinder can be subjected to chemical treatment in a solution containing thioglycollic acid, preferably 0.1M for 248 hours, preferably 18 hours. Following a brief wash in water, residual chemicals are removed by washing the cylinder in a buffered solution 48-96 hours. The solution is refreshed every 24 hours. Following a further wash in water the cylinder is freeze dried.

The biological properties of the dense keratin material were demonstrated in vitro and the biophysical properties were examined in vivo. In vitro, the material is not cytotoxic and supports the growth of human and sheep fibroblasts. In a similar manner to that outlined above for the porous matrices, direct contact of the porous material with cells, as described in ISO 10993-5, using sheep fibroblasts produced the following effects. Wells of polystyrene cell culture plates containing either the non-porous material or no material as a control were initially seeded with ~10,000 cells (0 hours). During the first 24 h post-seeding, the cultures experienced a lag time as evidenced by a decline in cell numbers. This phenomenon has been recognised in all assays performed and the drop is observed in control wells in addition to those containing the test materials. Experimentation has shown that this lag time lasts for less than 12 h and that the exponential phase of growth begins at this point. Population doublings occur approximately every 24 h-48 h with sub-confluency (approximately 80% confluency) marking the end of logarithmic growth. This corresponds to the end of the experimental time course (5 days or 120 h). Extended time-course experiments have indicated a plateau in cell growth shortly after this with full confluence of the culture. Contact inhibition and depletion of nutrients play a key role in limiting the growth rate at this point and the monolayer culture exhibits signs of cell death (i.e. loss of membrane integrity, reduction in cell numbers, vacuolisation of individual cells). During the assay, cells were witnessed to attach to the upper surface of the disks. By light microscopy, the morphological appearance of these cells was deemed similar on all substrates compared to the no-material control. Similar assays with human fibroblasts produced very similar results, with typical fibroblast growth curves occurring in the presence of the porous material and approximately 80% confluency reached after 120 hours in culture. The control wells had reached 100% confluency at this time.

The biophysical properties (modulus of elasticity, modulus of rupture, tensile strength) were tested by implanting the material treated with thioglycollic acid and manufactured as plates 12 mm length, 4 mm width, 3 mm depth subcutaneously in adult rats. The plates were removed from the rats at 1, 3, 6 and 12 weeks and the physical strengths evaluated. The modulus of elasticity showed a decrease of 40 to 70% over a period of 3 to 6 weeks. The loss in dry weight at these two times was 5 to 10% which was in agreement with our study in the sheep with plates of the porous material.

Another aspect of the invention is a tough, dense keratin material for use in the fixation of bone, constructed from the heated compression of multiple layers of keratin film. Keratin films are readily prepared from S-sulfonated keratin using methods such as those described in WO 03/018673. Keratin films can also be constructed using a solution of S-sulfonated keratin which contains a suspension of hydroxyapatite. Using this method hydroxyapatite is incorporated into keratin films at a level of 0-50% on mass of keratin. The films formed can be stacked into layers and compressed to a pressure in the range 10,000 to 100,000 kPa at a temperature in the range 50 to 200° C. for a time in the range 1 to 60 minutes. Following compression water is added to the compressed mixture and further compression occurs, under identical conditions. The resulting material contains an intimate mixture of keratin and hydroxyapatite in the form of a dense, tough block. Chemical treatment is then used to convert the S-sulfonate groups back to cystine. Thioglycollic acid or ammonium thioglycollate is used, under treatment and washing conditions identical to those described above. Once dry, the resulting material can be machined to a shape useful as a device in orthopaedic surgery, such as a screw or a pin.

In an alternative approach, chemical treatment is applied to keratin films containing hydroxyapatite at a level of 0-60% prior to stacking them into layers. Chemical treatment is achieved by soaking the films in a solution of ammonium thioglycollate of similar composition to that described above, for a period of 20-60 minutes. Multiple washing of the films in water removes residual chemical and on drying the resulting materials contain keratin with the S-sulfo group having been converted back to cystine. The films are then layered and compressed in a manner identical to that described above and the resulting material contains an intimate mixture of keratin and hydroxyapatite in the form of a dense, tough block. No further chemical treatment is needed, and the material can be machined to a shape useful as a device in orthopaedic surgery, such as a screw or a pin.

An aspect of the invention is the use of reducing agents, such as ammonium thioglycollate or thioglycollic acid described above, in order to remove the sulfonate functionality from the protein and restore the disulfide bonding originally present in the native keratin. In the sulfonate form the keratin is soluble above pH 4 and rapidly resorbed in vivo. In order to sustain the material for a longer time within the body, and control the rate of degradation and resorption of the material, reductive agents that remove the sulfonate function and crosslink the protein can be employed. The extent to which reductive agents are used, the time of exposure and concentration of reagents, affects the ratio of sulfonate groups to disulfide bonds present within the material. This in turn affects the strength and rate of degradation in vivo. Other crosslinking agents, such as those employed to modify the properties of other biological biomaterials, for example glutaraldehyde and ethyldimethylaminopropylcarbodiimide hydrochloride (EDC) which are used to modify the properties of collagen biomaterials, can also be used to modify the properties of the keratin biomaterials.

EXAMPLES

Example 1a

Porous Keratin Material 0.4 g of S-sulfonated keratin intermediate filament protein powder, ground to a particle size of 125-300 micron, is mixed with 0.5 ml of water and 0.024 g of sodium chloride and stand for 5 minutes. This mixture is packed into a 12 mm diameter die and pressed to a pressure of 15,000 kPa for 2 minutes. On removal from the die a 3 mm diameter cylinder is cut from the pellet and the cylinder is soaked in a chemical treatment solution, in order to wash out the porogen and leave a porous material, while also removing the sulfonate functionality from the keratin and restoring disulfide crosslinks to the protein. This chemical treatment may take one of two forms. Firstly, a solution of 0.25M ammonium thioglycollate containing 0.1M sodium phosphate buffered to pH 7.0 can be used to treat the cylinder for a period of 18 hours. Residual chemicals are removed by subsequent washing of the pellet in water successively for 10, 40 and 10 minute periods. After washing the cylinder is then freeze dried. Alternatively, the cylinder can be subjected to chemical treatment in a solution containing 0.1M thioglycollic acid for 18 hours. Following a brief wash in water, residual chemicals are removed by washing the cylinder in a solution of 0.1M TRIS 11.25 mM calcium chloride for 72 hours. The solution is refreshed every 24 hours. Following a further wash in water the cylinder is freeze dried.

Example 1b

Porous Keratin Material Containing Hydroxyapatite

Production of this material is identical to that described in example 1a, with the addition of 0.034 g hydroxyapatite at the same point as the inclusion of sodium chloride, to give the final product a level of 6% hydroxyapatite by mass.

Example 1c

Porous Keratin Material Containing Hydroxyapatite

In order to prepare a porous keratin material, a 5% keratin solution was prepared by suspending 0.5 g S-sulfonated wool keratin protein in water, followed by the gradual addition of 0.5 ml of 1M sodium hydroxide to the vigorously stirred solution over the approximately 2 hours. The pH of the solution was carefully monitored and observed to elevate to ~pH10 upon immediate addition of base, and gradually fall as the base was absorbed by dissolution of the protein. A final pH of 9.5 was obtained. The protein solution was centrifuged at 34,000 g to remove any insoluble material and 0.5 g of hydroxyapatite was thoroughly mixed into the solution. The mixture was frozen and freeze dried to produce a porous material. The material was immersed in an ammonium thioglycollate solution identical to that used in example 1a for 30 minutes, and subsequently washed in three batches of water for 20 minutes and freeze dried.

Example 2a

Dense Keratin Material 0.5 g of S-sulfonated keratin protein powder, ground to a particle size of 125-200 micron, is mixed with 0.5 ml of water and allowed to stand for 5 minutes. This mixture is packed into a 12 mm diameter die and pressed to a pressure of 15,000 kPa for 2 minutes. On removal from the die a desirable shape is cut from the pellet, such as a 12 mm by 4 mm block. The block is soaked in a chemical treatment solution, in order to remove the sulfonate functionality from the keratin and restore disulfide crosslinks to the protein. This chemical treatment may take one of two forms. Firstly, a solution of 0.25M ammonium thioglycollate containing 0.1M sodium phosphate buffered to pH 7.0 can be used to treat the block for a period of 18 hours. Residual chemicals are removed by subsequent washing of the block in water successively for 10, 40 and 10 minute periods. After washing the block is then allowed to dry in air at room temperature. Alternatively, the block can be subjected to chemical treatment in a solution containing 0.1M thioglycollic acid for 18 hours. Following a brief wash in water, residual chemicals are removed by washing the block in a solution of 0.1M TRIS 11.25 mM calcium chloride for 48 hours. The solution is refreshed every 24 hours. Following a further wash in water the block is dried in air at ambient temperature.

Example 2b

Dense Keratin Material Containing Hydroxyapatite

Production of this material is identical to that described in example 2a, with the addition of 0.032 g hydroxyapatite to the keratin powder at the start of the process, to give the final product a level of 6% hydroxyapatite by mass.

Example 2c

Dense Keratin Material Constructed from Keratin Films

Films of S-sulfonated keratin, of thickness 0.3 mm prepared by methods such as those outlined in WO 03/018673 were cut to 4×50 mm. A number of films of total mass 1 g (equivalent to 50 films) were stacked in layers in a heated steel block of internal dimensions 5×50 mm and pressed to a pressure of 50,000 kPa for 5 minutes, maintained at a temperature of 80-100° C. through heating of the steel block. The keratin block formed was immersed in the ammonium thioglycollate solution described in example 1a for 18 hours, and subsequently washed in water for 10,40,10 minutes. Air dry In a variation, the films used contained 50% hydroxyapatite and were prepared as follows: 1.0 g S-sulfonated wool keratin protein was suspended in water 0.2 g of Glycerol and 1.0 ml of 1M sodium hydroxide was gradually added to the vigorously stirred solution over the approximately 2 hours. The pH of the solution was carefully monitored and observed to elevate to ~pH10 upon immediate addition of base, and gradually fall as the base was absorbed by dissolution of the protein. A final pH of 9.5 was obtained. The protein solution was centrifuged at 27,000 g to remove any insoluble material. 1.0 g of hydroxyapatite was made into a paste with a small amount of 99% ethanol (~1 ml) and then thoroughly mixed in with the 5% solution. The mixture was cast on a 100 mm square petri dish and allowed to dry under ambient conditions.

Example 2d

Dense Keratin Material Constructed from Pretreated Keratin Films

Films of S-sulfonated keratin, of thickness 0.3 mm prepared by methods such as those outlined in WO 03/018673 were treated in the solution of ammonium thioglycollate described in example 1a for 30 minutes. Following treatment the films were washed in water and dried to leave films containing disulfide rather than S-sulfonate functionality. These films were cut to 4×50 mm. A number of films of total mass 1 g (equivalent to 70 films) were stacked in layers in a heated steel block of internal dimensions 5×50 mm and pressed to a pressure of 50,000 kPa for 5 minutes, maintained at a temperature of 80-100° C. through heating of the steel block. Remove the keratin block and briefly soaked in water and press into the heat block and compress for 20,000 kpa for 5 minutes. Heat the block to 80-100° C. under pressure. Press to 30,000 kPa for 30 minutes.

In a variation, the films used contained 50% hydroxyapatite and were prepared as described for example 2b. Dense keratin material with hydroxyapatite were prepared as same as 2c Where in the foregoing description, reference has been made to specific components or integers of the invention having known equivalent, then such equivalents are herein incorporated as if individually set forth.

INDUSTRIAL APPLICABILITY

The invention will be useful in the medical field, especially in the area of bone injury. Keratin materials according to the invention are biocompatible and can be used as bone replacement and augmentation products.

The product can be used for example to replace bone lost due to clinical conditions such as trauma or tumors and will promote healing by acting as a scaffold for the laying down of new bone. The porous keratin scaffold is resorbed and replaced by new woven bone which will subsequently be remodelled into cancellous and cortical bone.

The invention claimed is:

1. A porous spongy material for bone grafting application comprising S-sulfonated keratin and hydroxyapatite in a weight ratio of S-sulfonated keratin to hydroxyapatite ranging from 1:0.1 to 1:2, respectively, where the S-sulfonated keratin is optionally treated with a reducing agent to remove sulfonate functionality and provide disulfide crosslinks.

2. A process for preparing the porous spongy material of claim 1 comprising the steps of forming an aqueous solution of S-sulfonated keratin, suspending hydroxyapatite in the S-sulfonated keratin solution at a weight ratio of S-sulfonated keratin to hydroxyapatite ranging from 1:0.1 to 1:2, respectively, and then freeze drying.

3. The process of claim 2 comprising the additional steps of treating the freeze dried material with a reducing agent to remove sulfonate functionality from the S-sulfonated keratin and form disulfide crosslinks, washing to remove the reducing agent and freeze drying the washed material.

* * * * *